US012799122B2

(12) United States Patent
Cahana et al.

(10) Patent No.: US 12,799,122 B2
(45) Date of Patent: Nov. 17, 2026

(54) METHODS FOR SYNTHESIS OF AN ADVANTAGEOUS N-HETEROCYCLIC CARBENE CATALYST

(71) Applicant: XF Technologies Inc., Edgewood, NM (US)

(72) Inventors: Aviad Cahana, Kula, HI (US); William A Farone, Irvine, CA (US)

(73) Assignee: XF BIOSOLUTIONS, LLC, Miami, FL (US)

( * ) Notice: Subject to any disclaimer, the term of this patent is extended or adjusted under 35 U.S.C. 154(b) by 444 days.

(21) Appl. No.: 18/491,765

(22) Filed: Oct. 21, 2023

(65) Prior Publication Data

US 2024/0059701 A1 Feb. 22, 2024

Related U.S. Application Data

(63) Continuation of application No. PCT/US2022/025147, filed on Apr. 16, 2022.

(60) Provisional application No. 63/178,381, filed on Apr. 22, 2021.

(51) Int. Cl.

| | |
|---|---|
| ***C07D 487/04*** | (2006.01) |
| ***B01J 31/02*** | (2006.01) |
| ***C07C 241/02*** | (2006.01) |
| ***C07D 207/22*** | (2006.01) |
| ***C07D 307/68*** | (2006.01) |

(52) U.S. Cl.
CPC ........ *C07D 487/04* (2013.01); *B01J 31/0271* (2013.01); *C07C 241/02* (2013.01); *C07D 207/22* (2013.01); *C07D 307/68* (2013.01)

(58) Field of Classification Search
None
See application file for complete search history.

(56) References Cited

U.S. PATENT DOCUMENTS

| | | | | |
|---|---|---|---|---|
| 3,966,900 | A | 6/1976 | Hennart | |
| 8,710,250 | B2 * | 4/2014 | Mikochik ............ | C07D 307/68 549/484 |
| 9,108,940 | B2 * | 8/2015 | Mikochik ............ | C07D 307/68 |
| 2004/0029947 | A1 | 2/2004 | Gopalsamy | |
| 2010/0210452 | A1 | 8/2010 | Bode | |
| 2011/0294840 | A1 | 12/2011 | Ihara | |
| 2014/0206886 | A1 | 7/2014 | Scheidt | |

OTHER PUBLICATIONS

Dhayalan et al., Synthesis 2019; 51(14): 2845-2864 (Year: 2019).*

* cited by examiner

*Primary Examiner* — Jeffrey S Lundgren
(74) *Attorney, Agent, or Firm* — Gerald Grafe

(57) ABSTRACT

The present invention concerns the synthesis of the salts of a Triazolium N-Heterocyclic Carbene (NHC) catalyst in various salt forms prepared from 2-methylaniline, 2-methylphenylhydrazine hydrochloride or 2-methylphenylhydrazine. The molecules so prepared are useful in catalysis of carbene reactions and are advantageous due to their lack of chlorinated or fluorinated intermediates and lack of chlorine or fluorine in the final structure.

20 Claims, 9 Drawing Sheets

$C_{13}H_{18}N_3O_4S$

Formula 1

$C_{13}H_{18}N_3O_4S$

Formula 1

$C_{12}H_{19}N_3O_4S$

Formula 2

$C_7H_9N$ $C_7H_{10}ClN$ $C_{11}H_7BF_9N_3$

Formula 3

METHODS FOR SYNTHESIS OF AN ADVANTAGEOUS N-HETEROCYCLIC CARBENE CATALYST

TECHNICAL FIELD

The present invention concerns the synthesis of the salts of a Triazolium N-Heterocyclic Catalyst in various salt forms prepared from 2-methylaniline, 2-methylphenylhydrazine hydrochloride or 2-methylphenylhydrazine. The molecules so prepared are useful in catalysis of carbene reactions and are advantageous due to their lack of chlorinated or fluorinated intermediates and lack of chlorine or fluorine in the final structure increasing biodegradability and reducing toxicity.

BACKGROUND ART

N-Heterocyclic Carbene (NHC) catalysts have been shown to be useful in various chemical reactions. The generation of commodity chemicals from renewable feedstocks is a continuing priority in the field of sustainable green chemistry. Chemical processes that operate in a catalytic fashion with catalysts that are biodegradable, of low toxicity and economical to synthesize on a commercial scale are extremely desirable for sustainability.

The utility of such catalysts is exemplified by the use in synthesis of 5-methyl-2-furoic acid derivatives made from 5-(chloromethyl)-2-furaldehyde. This utility is discussed in detail in U.S. Pat. Nos. 8,710,250 and 9,108,940, which are incorporated herein by reference.

NHC catalysts function in reactions by cycling between the carbene and the reagents being targeted. This recycling allows a small amount of catalyst to be used to synthesize a large amount of product all at high yield. The catalyst binds to the substrate and converts an electrophilic carbon into a nucleophilic carbon for the reaction and is then released to perform the function once again.

The economic value of the NHC catalyst can be related to the ratio of the catalyst to the reagents required for the reaction and to the overall yield including any side or by-product reactions. Embodiments of the present invention provide methods for the synthesis and use of an NHC that has been found to allow surprisingly high yields in reactions such as described in U.S. Pat. Nos. 8,710,250 and 9,108,940. The synthetic procedure described produces the NHC catalyst from readily available compounds that contain no chlorine or fluorine thus making the catalyst and the synthesis process environmentally favorable.

SUMMARY OF THE INVENTION

In one example embodiment, the present invention provides a method for preparing the NHC catalyst of Formula 1 (FIG. 1) through a series of steps starting from 2-methylaniline. The method includes (a) contacting 2-methylaniline with aqueous hydrochloric acid to form the amine chloride while maintaining the temperature locally (e.g., 250 cc volumes), including where the chemicals are contacted, at 0-5 °C; (b) contacting the amine chloride in solution with a diazotization reagent to form the diazonium chloride salt while maintaining the temperature locally (e.g., 250 cc volumes), including where the chemicals are contacted, at 0-5 °C; (c) adding a reducing agent to convert the diazonium chloride salt to 2-methylphenylhydrazine hydrochloride while maintaining the temperature locally (e.g., 250 cc volumes), including where the chemicals are contacted, at 0-5 °C; (d) filtering to recover the 2-methylphenylhydrazine hydrochloride salt as a solid; (e) contacting the recovered 2-methylphenylhydrazine hydrochloride salt with an aqueous base to form the free 2-methylphenylhydrazine; (f) extracting the 2-methylphenylhydrazine from the aqueous basic solution with an organic solvent to provide a solution of the 2-methylphenylhydrazine in the organic solvent; (g) drying the solution of 2-methylphenylhydrazine by addition of a drying agent; (h) removing the drying agent by filtration; (i) contacting the dry 2-methylphenylhydrazine solution with the reaction products of 2-pyrrolidine and dimethylsulfate to make the iminohydrazone of Formula 2 (FIG. 2) in an organic solvent; (j) distilling the solution of the iminohydrazone of Formula 2 to remove excess solvents; (k) recovering the iminohydrazone of Formula 2 as a salt; (l) contacting the iminohydrazone salt of Formula 2 with an organic solvent and trimethylorthoformate to make the methylsulfate salt of the N-Heterocyclic Carbene catalyst of Formula 1; (m) recovering the N-Heterocyclic Carbene catalyst of Formula 1 as a salt.

In one example embodiment, the present invention provides a method for preparing the NHC catalyst of Formula 1 through a series of steps starting from 2-methylphenylhydrazine hydrochloride. The method includes (a) contacting the 2-methylphenylhydrazine hydrochloride salt with an aqueous base to form the free 2-methylphenylhydrazine; (b) extracting the 2-methyl phenylhydrazine from the aqueous basic solution with an organic solvent to provide a solution of the 2-methylphenylhydrazine in the organic solvent; (c) drying the solution of 2-methylphenylhydrazine by addition of a drying agent; (d) removing the drying agent by filtration; (e) contacting the dry 2-methylphenylhydrazine solution with the reaction products of 2-pyrrolidine and dimethylsulfate to make the iminohydrazone of Formula 2 in an organic solvent; (f) distilling the solution of the iminohydrazone of Formula 2 to remove excess solvents; (g) recovering the iminohydrazone of Formula 2 as a salt; (h) contacting the iminohydrazone salt of Formula 2 with an organic solvent and trimethylorthoformate to make the methylsulfate salt of the N-Heterocyclic Carbene catalyst of Formula 1; (i) recovering the N-Heterocyclic Carbene catalyst of Formula 1 as a salt.

In one example embodiment, the present invention provides a method for preparing the NHC catalyst of Formula 1 through a series of steps starting from 2-methylphenylhydrazine. The method includes (a) contacting the 2-methylphenylhydrazine solution with the reaction products of 2-pyrrolidine and dimethylsulfate to make the iminohydrazone of Formula 2 in an organic solvent; (b) distilling the solution of the iminohydrazone of Formula 2 to remove excess solvents; (c) recovering the iminohydrazone of Formula 2 as a salt; (d) contacting the iminohydrazone salt of Formula 2 with an organic solvent and trimethylorthoformate to make the methylsulfate salt of the N-Heterocyclic Carbene catalyst of Formula I; (e) recovering the N-Heterocyclic Carbene catalyst of Formula 1 as a salt.

DETAILED DESCRIPTION

The detailed description as set forth below is intended as a description of example embodiments of the invention and is not intended to represent the only form in which the present invention can be constructed or utilized. The description sets forth example function and sequences of steps for constructing and operating the invention. Since the method comprises many steps it is to be understood that the same or equivalent functions and sequences can be accomplished by different embodiments and they are intended to be encompassed within the scope of the invention. For example, there are points in the invention where intermediate chemicals are collected to be utilized in further steps. This allows for apparatus of differing size capacity to be used in the subsequent steps and allow for the assessment of the purity and quality of the intermediate collected chemicals. As a further example, the relative weights of the ingredients can be varied to account for levels of purity.

Figure 1:
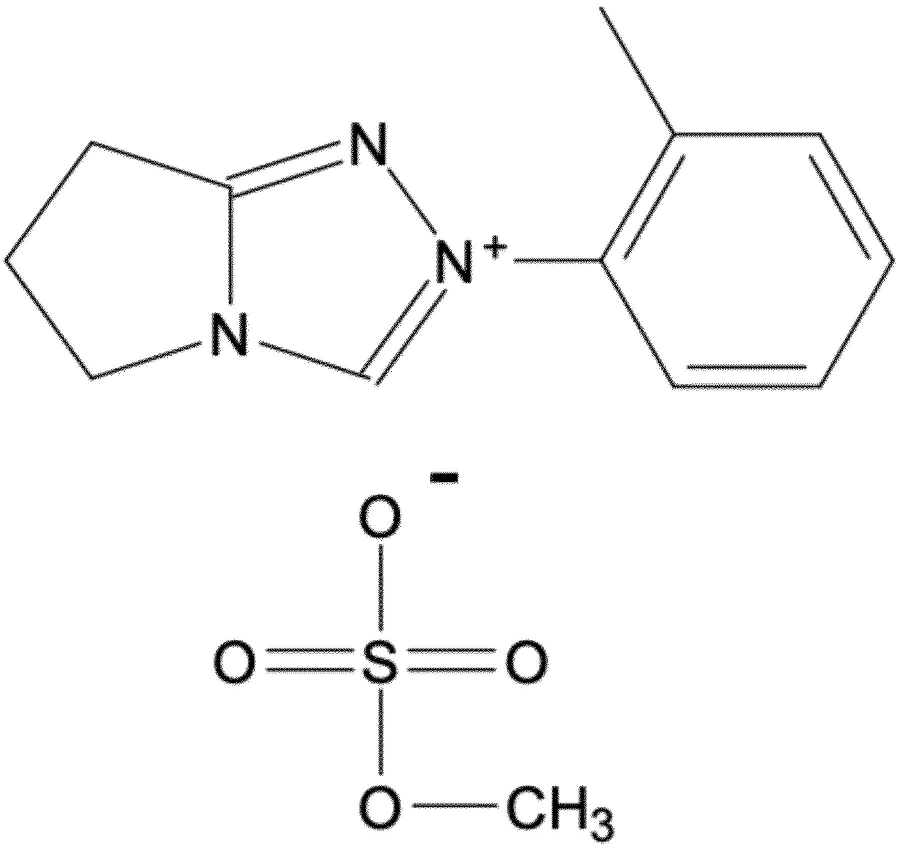
FIG. 1 illustrates the molecule of Formula 1.
Figure 2:
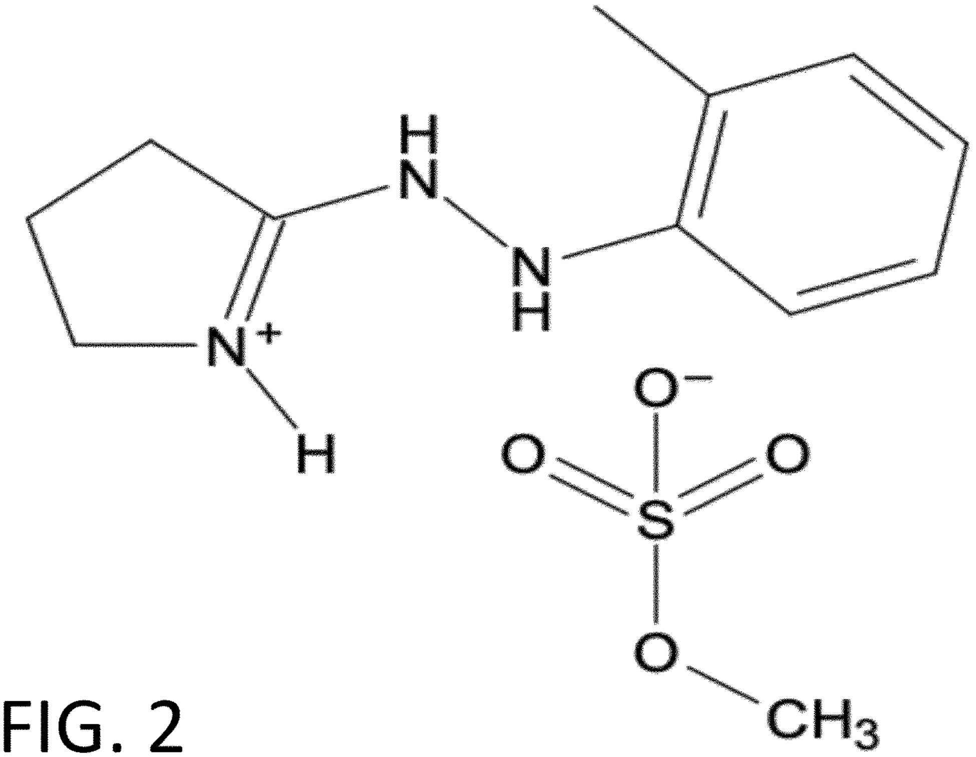
FIG. 2 illustrates the molecule of Formula 2 which is the iminohydrazone precursor to the molecule of Formula 1.
Figure 3:
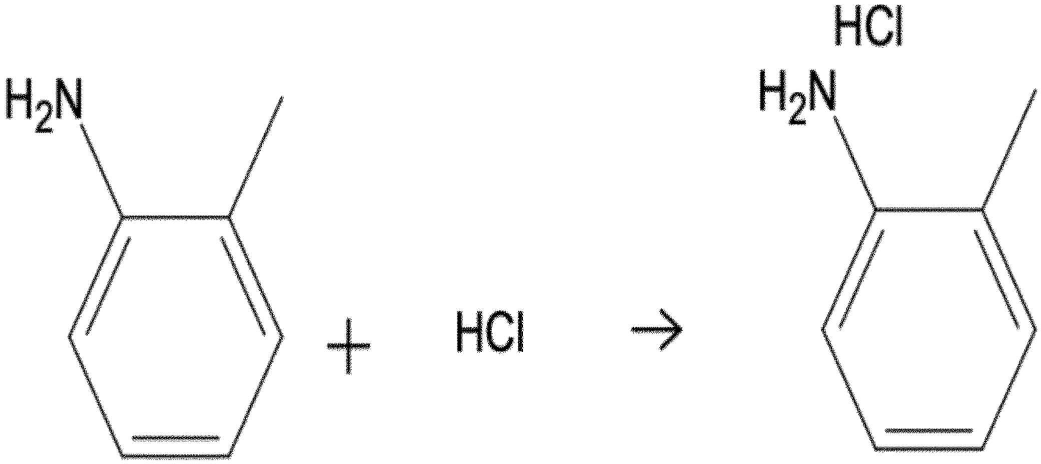
FIG. 3 illustrates the reaction of 2-methylaniline with hydrochloric acid to produce 2-methylaniline hydrochloride.
Figure 5:
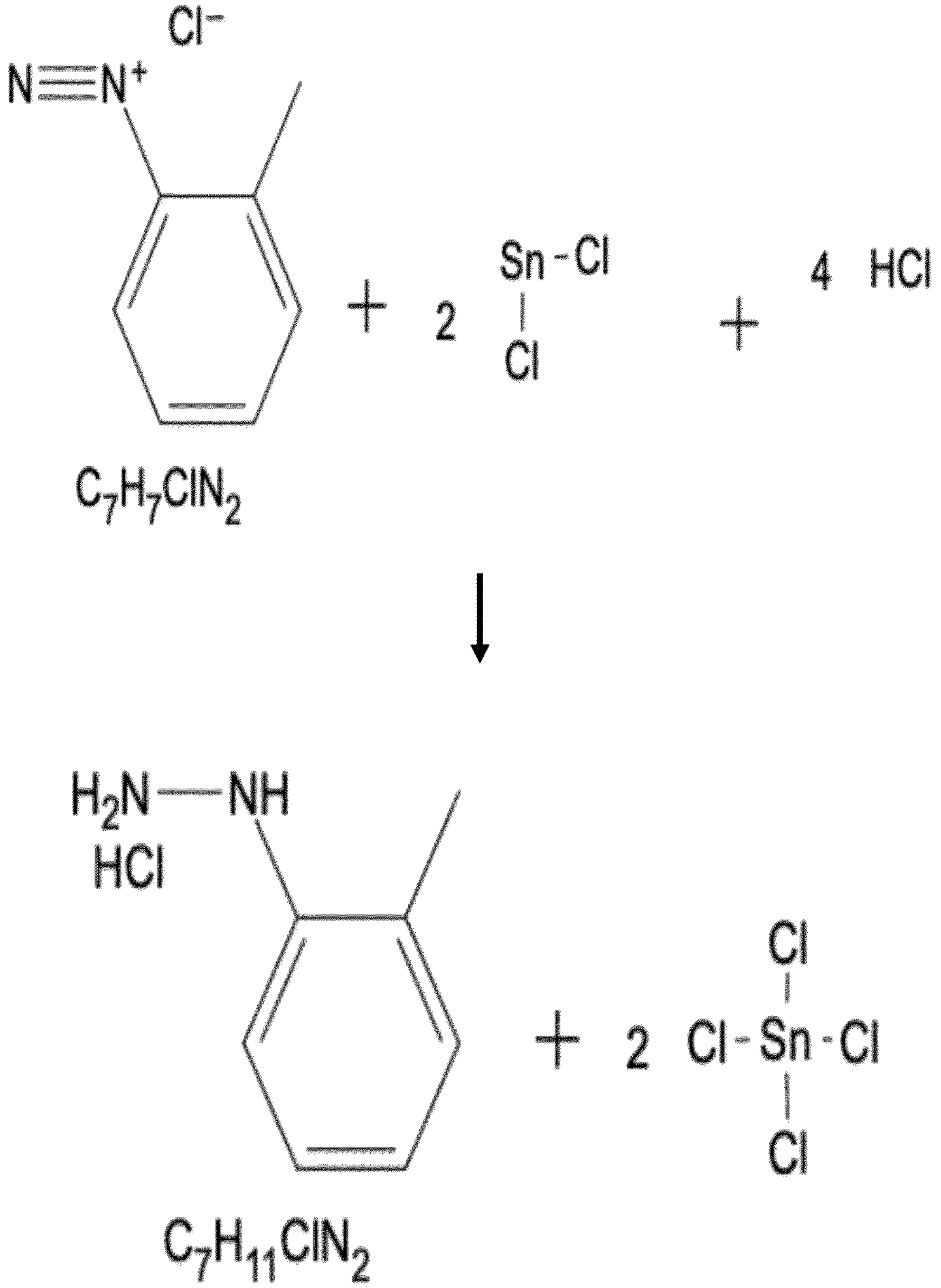
FIG. 5 illustrates the reaction of the diazonium salt with stannous chloride and hydrochloric acid to produce 2-methylphenylhydrazine hydrochloride.
Figure 6:
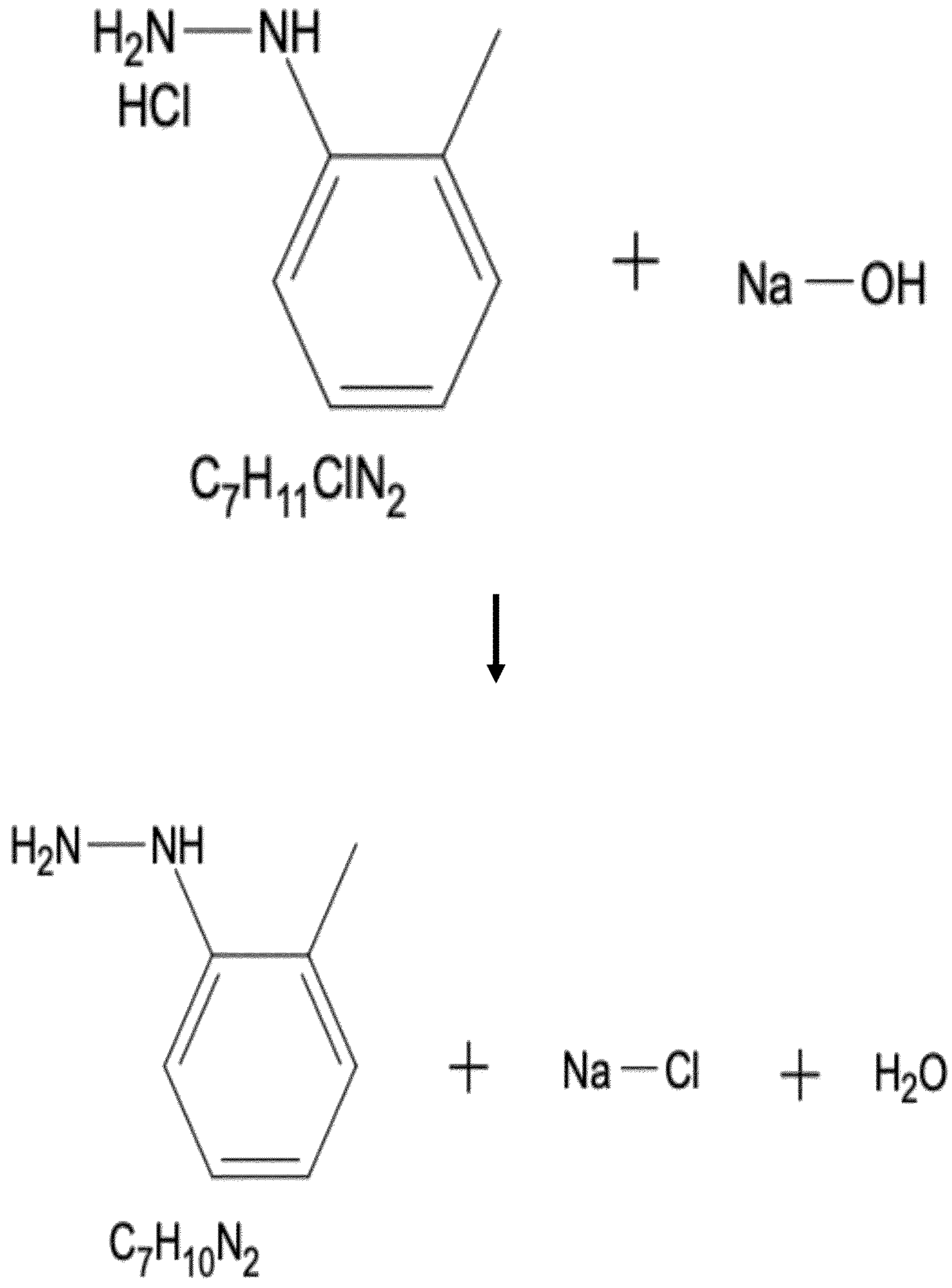
FIG. 6 illustrates the reaction of 2-methylphenylhydrazine hydrochloride with sodium hydroxide to produce 2-methylphenylhydrazine.

Based on the ability to store intermediate chemicals, the steps of the method can be grouped into stages. In the first stage a 2-methylphenylhydrazine hydrochloride is produced from the reactions indicated in FIGS. 3-5. In the second stage 2-methylphenylhydrazine is produced from the reaction indicated in FIG. 6. In the third stage the iminohydrazone precursor is produced from the reactions indicated in FIGS. 7-8. In the fourth stage the NHC catalyst is produced (FIG. 9). Each stage involves operations that can occur in individual reactors and related equipment.

A method for producing the NHC of Formula 1 can proceed from three different starting chemicals depending on the commercial economics and their availability. Three potential starting chemicals are 2-methylaniline (requiring all 4 stages), 2-methylphenylhydrazine hydrochloride (requiring stages 2-4) and 2-methylphenylhydraziine (requiring stages 3-4). The 2-methylphenylhydrazine hydrochloride can be made from the 2-methylaniline and the 2-methylphenylhydrazine can subsequently be made from the 2-methylphenylhydrazine hydrochloride.

Any method comprising a series of sequential chemical reactions benefits from the highest optimized yields in each step. For a preferred yield, highest quality and maximum flexibility the method is preferably performed starting from the 2-methylaniline. The series of reactions leading from the 2-methyl aniline to the 2-methylphenylhydrazine (FIGS. 3-6, stage 1 and stage 2) are related to the synthesis of phenylhydrazine from aniline first reported as early as 1875 by Emil Fischer, "Ueber aromtatische Hydrazinverbindigen", *Berichte der deutscen chemischen Gesellschaft,* 8, 589-594, incorporated herein by reference. Variants on this process are used commercially to produce related compounds. The steps in the present invention are significantly different from that in the reference, due to the difference in the chemical structures, the need for high yields and the desire for a more environmentally favorable process. The reactions in the current method starting from 2-methylaniline are highly exothermic and the generated heat can destroy the intermediates in the reaction sequence leading to lower yields, impurities and higher costs. It is preferable to produce the chemicals of stage 1 and stage 2 by the techniques of the current method for both quality and cost.

Description of Stage 1.

Figure 4:
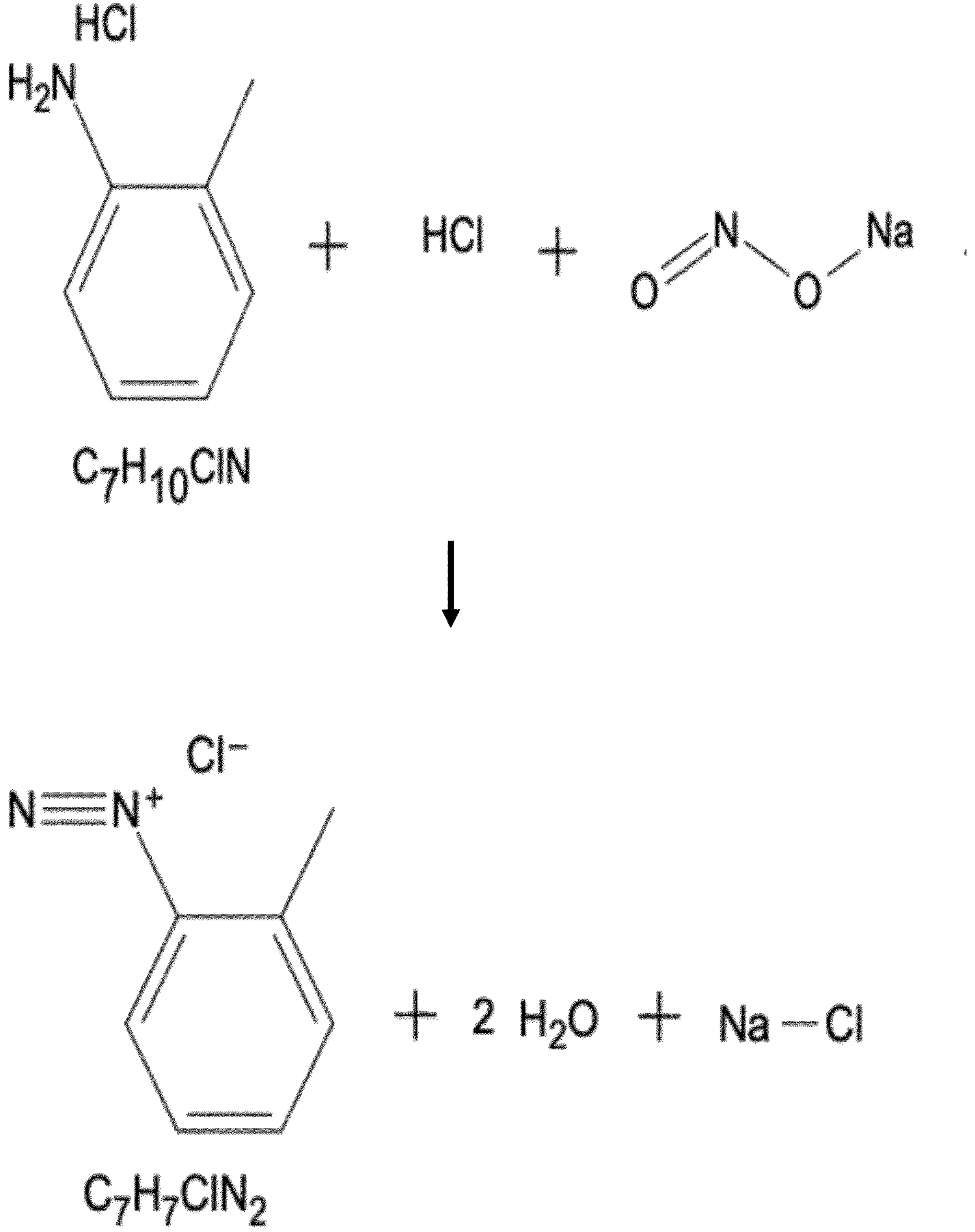
FIG. 4 illustrates the reaction of 2-methylaniline hydrochloride with sodium nitrite and hydrochloric acid to produce the diazonium salt.

In stage 1 (FIGS. 3-5), as the amount of chemical desired increases, it can be useful to tightly control the heat transfer from the reaction vessel so that the temperature stays in the range of about 0-5 °C. If the temperature is above that range, yield and product purity can suffer dramatically. If the temperature is below that range, the reaction slows, and the kinetics can be difficult to maintain. To maintain the reaction kinetics the 2-methylaniline can be added in the reaction of FIG. 3 in about 45-50 minutes and the reaction can be completed in 1 hour from the beginning of the addition. The addition of $NaNO_2$ in the reaction of FIG. 4 is added in about 45-50 minutes and the reaction can be completed in 2 hours from the beginning of the addition. The reduction using the $SnCl_2$ can be completed in 2 hours and the reaction can be completed in 3 hours from the beginning of the addition. Cooling systems unable to maintain these rates and times can decrease the yield. Locally generated heat at the site of adding chemicals can also cause degradation even when the bulk temperature is within the range. To avoid these problems with the reaction kinetics, the agitation and heat transfer, particularly in large vessels is preferred to have internal cooling such that locally reactive mixing is near a cooling surface that can remove heat at a rate that matches the desired addition rate. Since the reaction occurs in hydrochloric acid media and involves highly reactive intermediates that can react with most metals, the materials of construction have to be carefully selected. Thin coatings of polymeric material on metal cooling coils or titanium or Hastelloy metal coils can be used.

The product output of stage 1 (FIG. 5) is collected by filtration. It can then be vacuum dried for use in further stages. The vacuum drying can include air scrubbing to eliminate hydrochloric acid fumes reaching the vacuum pump or the atmosphere. The filtrate liquid is high in $Sn(Cl)_4$. To recover the Sn, the filtrate can be neutralized with aqueous sodium hydroxide to a pH of about 7.5, whereupon $Sn(OH)_4$ precipitates, the residual water thus having a Sn content well below 10 mg/L (ppm). The $Sn(OH)_4$ can then be dried to $SnO_2$ as a source for making tin metal. This reprocessing is environmentally sound and cost effective. An alternate reductant that can be used in stage 1 is sodium bisulfite. That reductant is used in the production of phenylhydrazine from aniline. It requires a long heating step that $SnCl_2$ does not require and it is not currently economically recyclable.

A typical stage 1 reaction sized for the production of up to 0.2 gram-mole (24.4 grams) uses a 1-liter reaction flask fitted with a magnetic stirrer. At the 1-liter level, an internal coil of 304 stainless steel tightly contained within linear low-density polyethylene tubing can be used to maintain the desired addition rates and reaction temperature range when it is internally cooled with −10 °C fluid. The flask is also cooled with the same fluid. Most of the reaction is carried out at 0 °C and the reaction is kept in the range of 0-5 °C, preferably never exceeding 5 °C until after the reaction is completed. To the flask are added 128 mL of concentrated HCl and 72 mL of water. All subsequent additions are made below the surface of the liquid in the reactor near the stirrer. When the temperature reaches about 0 °C, 21.4 grams of 2-methylaniline precooled to 0-5 °C can be added slowly over about 50 minutes maintaining the 0-5 °C range. An additional 10 minute (one-hour elapsed time) is allowed for the formation of the amine chloride. A precooled solution (0-5 °C) of 13.8 grams of sodium nitrite, $NaNO_2$, in 32 mL of water is then added over about 50 minutes maintaining the 0-5 °C range. The reaction is allowed to complete in the next 70 minutes; 2 hours from the beginning of $NaNO_2$ addition. A precooled solution (0-5 °C) of 76 grams of $SnCl_2$ in 60 mL of 31% by weight HCl plus 140 mL of water (about 200 mL total), is added slowly over the next 2 hours maintaining the 0-5 °C range. The reaction can then be allowed to complete for the next hour. The precipitate is filtered, and the filter cake washed with about 50 mL of a solution of 15 mL of 31% by weight HCl plus 35 mL of water. The cake is vacuum dried at about 40 °C. The filtrate is collected and saved for reprocessing the $SnCl_4$.

Description of Stage 2.

In stage 2, the 2-methylphenylhydrazine hydrochloride is converted to 2-methylhydrazine by treatment with aqueous sodium hydroxide in a 10-20% solution. It is conveniently extracted from the aqueous phase with a non-water miscible solvent wherein that solvent will be used for further stages. The 2-methylphenylhydrazine in the solvent is dried by addition of drying media such as zeolites or anhydrous sodium sulfate. For example, if the selected solvent is toluene, the amount of water in the solvent will be 0.5-0.6 grams per liter and can be quickly and easily removed. The stage 2 treatment also affords a means of purification of the 2-methylphenylhydrazine. Water soluble and base reactive compounds will be removed as they will remain in the aqueous phase.

Stage 2 can be performed at many scales depending on the amount of 2-methylphenylhydrazine hydrochloride one wishes to treat. The reaction used is based on each 100 grams of the crude 2-methylphenylhydrazine hydrochloride. The size of the vessel is therefore dependent on the size of the crude material treated. Approximately 500 mL of volume can be suitable for each 100 grams. About 250 mL of a 25% solution of sodium hydroxide, NaOH, is placed in a 500 mL flask outfitted with stirring and heating. The 100 grams of the hydrazine hydrochloride is added with stirring to the NaOH solution. The temperature is set to about 45 °C. While stirring is continued, about 250 mL of room temperature toluene is added. This should cool the system below 45 °C. All stirring can be stopped to allow the layers to separate. The layers can be separated by gravity separation. About 5 grams of anhydrous $Na_2SO_4$ can be added to the toluene solution. The solution can be mixed for about 30 minutes then stopped allowing the $Na_2SO_4$ hydrate to settle. The solution can be filtered to collect the filtrate and the filter cake washed with some toluene. The product is the solution of 2-methylphenyl hydrazine in toluene. As an example, yields of 90-95% can be achieved.

Description of Stage 3

Figure 10:
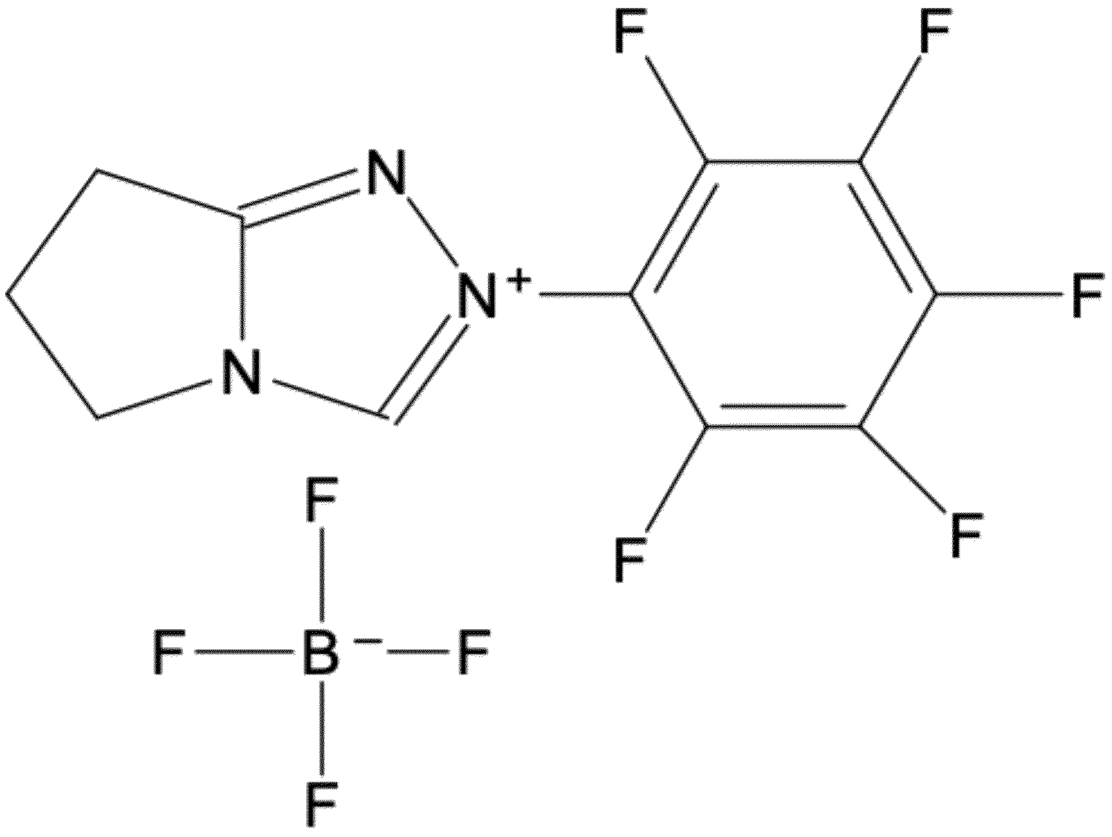
FIG. 10 illustrates the molecule of Formula 3.

The stage 3 reaction starts with the reaction of 2-pyrrolidine with the dimethylsulfate (FIG. 7) to produce the intermediate. This reaction can be performed in the same solvent used in stage 2, for example toluene, such that the 2-methylphenylhydrazine can simply be added as a solution in the same solvent. Alternate chemicals can be used in place of the dimethylsulfate. Trimethyloxonium tetrafluoroborate is an example of such an alternate chemical. The typical triazolium NHC of FIG. 10 was synthesized using the tetrafluoroborate which remains as the NHC anion. Not only is the reagent more difficult to use due to its toxicity, but it adds extra fluorine to either the disposal or attempted recovery of the catalyst after the catalyst is used. NHC catalysts undergo some degradation during use and thus the ultimate environmental fate of the NHC has to be considered in any commercial process using these compounds.

Figure 7:
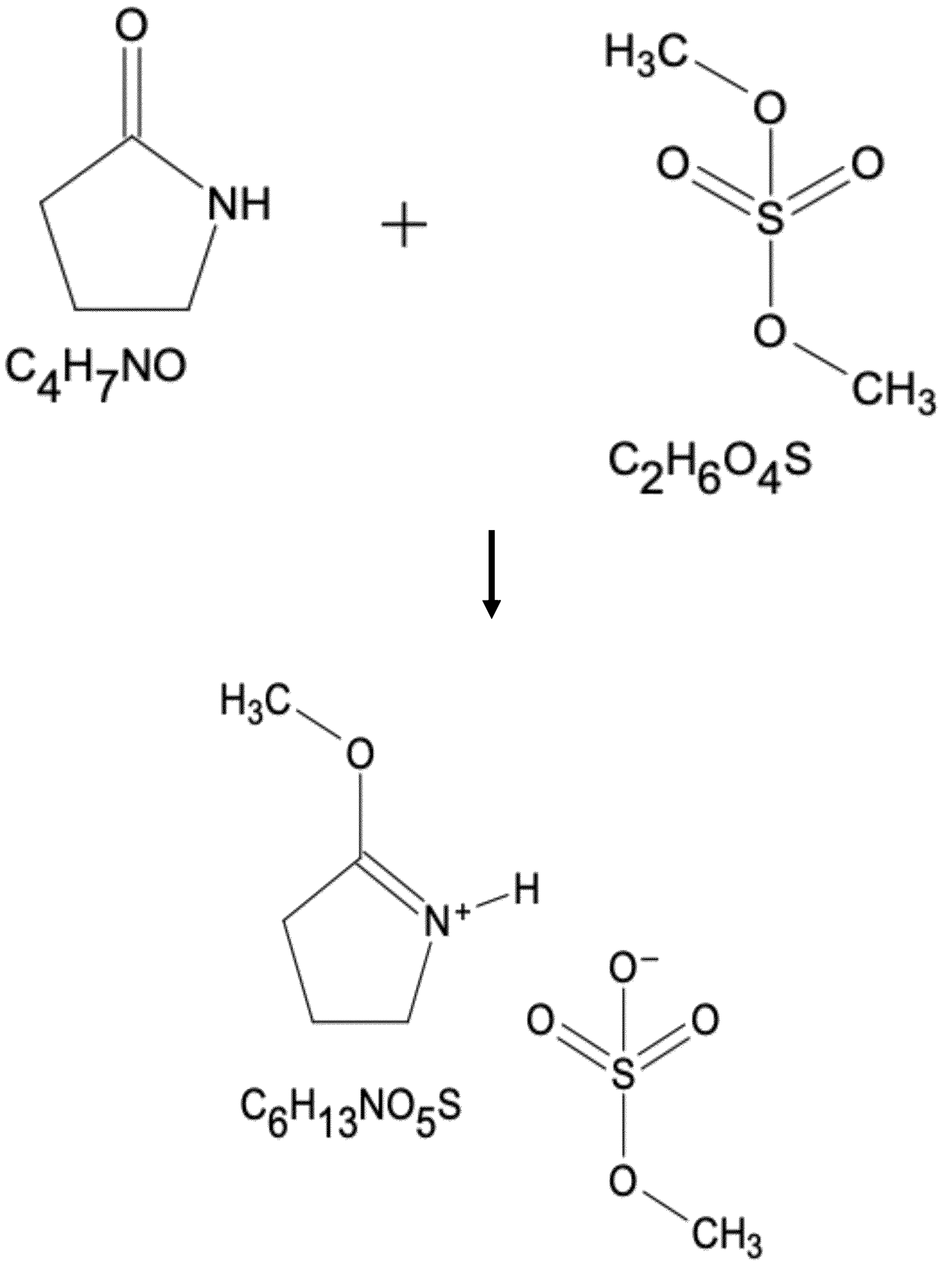
FIG. 7 illustrates the reaction of 2-pyrrolidine with dimethyl sulfate to produce the intermediate precursor for the iminohydrazone.
Figure 8:
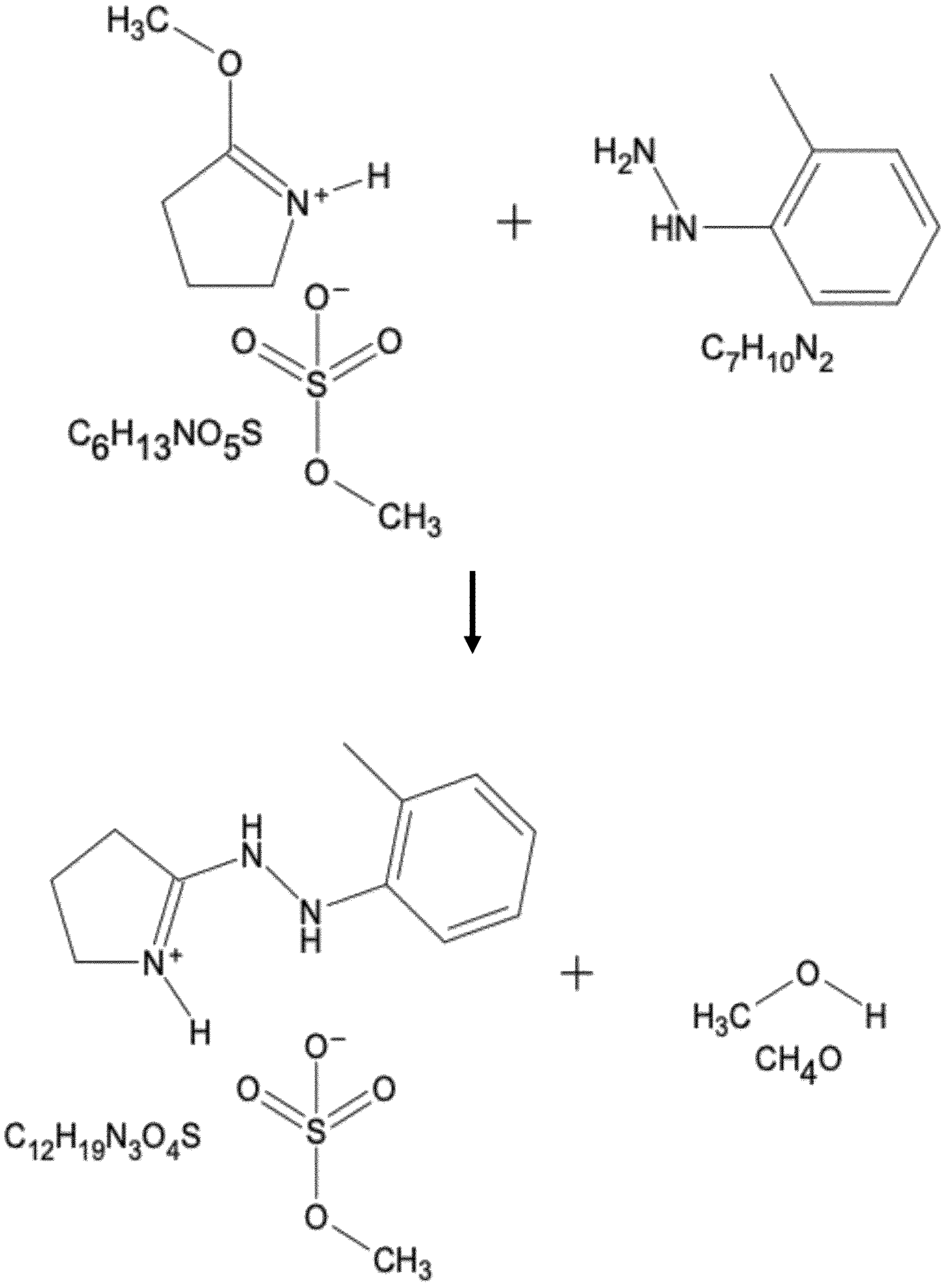
FIG. 8 illustrates the reaction of the intermediate precursor with 2-methylphenylhydrazine to produce the iminohydrazone.
Figure 9:
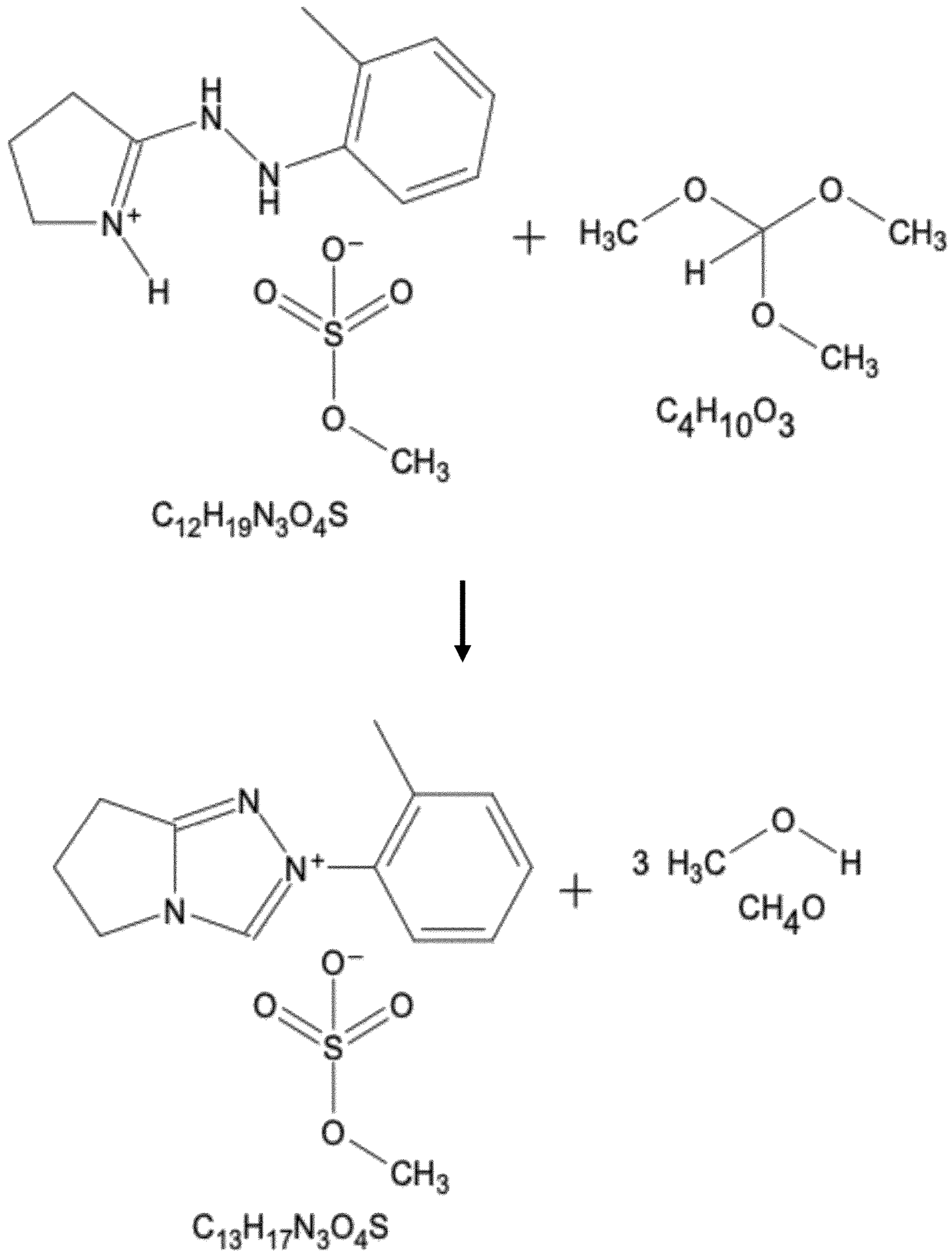
FIG. 9 illustrates the reaction of the iminohydrazone with trimethylorthoformate to produce the desired NHC of Formula 1.

The product of stage 3 is the iminohydrazone precursor to the NHC as shown in FIG. 8 after the reaction of the 2-methylphenylhydrazine with the intermediate formed in the reaction of FIG. 7. The methanol that is formed can be stripped from the reaction mixture when the mixture is vacuum distilled. When toluene is used as the solvent, the methanol-toluene azeotrope can be removed in early fractions and then the toluene. When the toluene concentration remaining is very low, and the product begins crystalizing, the product can be washed with ethyl acetate or a similar solvent to complete the crystallization. The solvent preferably is a solvent that does not form an azeotrope with toluene. This allows for ease of recovery by distillation of both solvents after the product is filtered from the solvents. The iminohydrazone precursor can then be vacuum dried and stored for use in stage 4.

A typical small-scale reaction for stage 3 is performed in a 2 or 3-liter vessel. The vessel is set up with a distillation column to be able to reflux solvents during the reaction and then, when the reaction is completed, to be able to vacuum distill the solvent, e.g., toluene. The vessel has stirring and heating. One liter (about 867 grams) of toluene is added to the reaction flask. Next, 35 grams of 2-pyrrolidone, $C_4H_7NO$, is added. Next, 52 grams of dimethyl sulfate is added. The flask is heated with stirring for 4 hours at 80 °C. The heating is stopped, and the vessel and contents allowed to cool to room temperature. Then 50 grams of 2-methylphenylhydrazine dissolved in toluene is added. The vessel is heated for 5 hours at 80 °C. The heating is stopped, and the vessel is cooled to room temperature. Vacuum is applied at about 20-30 Torr pressure while the temperature is maintained at about 20 °C. The solvent is removed in fractions to recover a first fraction that contains the methanol along with some toluene and then a toluene fraction. The temperature can be increased slightly if needed until only about 200-250 mL of solvent remains. The distillation is stopped and about 400 mL of ethyl acetate is added. The precursor product is the solid that is recovered by filtration. The filtrate is saved for recovery. The product can then be vacuum dried to be used in stage 4.

Description of Stage 4.

In stage 4 the iminohydrazone precursor of stage 3 is reacted with trimethylorthoformate in a suitable solvent to form the desired NHC catalyst (FIG. 9). A solvent like toluene can be used for all of the stages that require a solvent thereby decreasing solvent storage and allowing recovery and reuse of the same solvent within the facility for the overall process. At the completion of the reaction, excess trimethylorthoformate and solvent can be recovered by vacuum distillation and the product washed with a suitable solvent in which the product is not soluble. The product can be filtered, recovered and dried under vacuum. The filtrate can be reprocessed for reuse of the solvent and the residual trimethylorthoformate. The product of this stage is the final NHC of Formula 1.

A typical reaction for stage 4 can be carried out in a 20-22 liter reactor. The reactor is set up with a reflux column and connection to a receiver through a condenser such that it can be used for vacuum distillation. The reactor is fitted with stirring and a means of providing controlled heat. About 10-11 kg of toluene is added to the reactor. Next, 693 grams of the iminohydrazone precursor from stage 3 is added. Next, 1.3 kg of trimethylorthoformate (TMOF) is added. Heat is applied to maintain about 100 °C and a good reflux of the TMOF and toluene. The reaction is continued for 12-18 hours. When the reaction is completed, the system can be switched to distillation and about ⅔ of the volume in the reactor can be removed. This is approximately 7 liters. As vacuum is applied the temperature can be lowered to match a brisk distillation rate without flooding the distillation column. When the solvent has been removed, leaving 3-4 liters of volume, an approximately equal volume of ethyl acetate can be added and the product allowed to complete crystallization. The solids formed can be filtered and can be washed with an additional amount of ethyl acetate (approximately 1 liter). The solid product can be dried under vacuum with no heat to remove residual solvent. The filtrate can be saved for reprocessing to recover the ethyl acetate and toluene. Yields of 70% can be achieved.

INDUSTRIAL USE

The NHC catalyst of Formula 1 can be used in chemical reactions in a similar manner as any NHC catalyst. In methods to produce methyl-2-methyl-5-furoate, as that described in U.S. Pat. Nos. 8,710,250 and 9,108,940, it can be more effective that the NHC of FIG. 10. While the weight ratio usage of the NHC of this invention is similar or slightly less, the yield of the reaction with the NHC of Formula 1 can be higher and less by-products are generated. The NHC catalyst of Formula 1 can be also be used at a lower weight ratio than 5 other NHCs tested in the same furoate ester reactions.

Example 1. The Production of the 2-Methylphenylhydrazine Hydrochloride from 0.05 Gram-Moles of 2-Methylaniline The reaction was sized for a 250 mL reaction flask fitted with a magnetic stirrer. The flask was cooled with a −10 °C to −15 °C bath. The reaction was carried out in the range of 0-5 °C, never exceeding 5 °C. The quantities of 32 mL of concentrated (31% by weight) HCl and 18 mL of water were added to the flask. All subsequent additions were made below the surface to the liquid in the reactor near the stirrer. When the temperature reached about 2-3 °C, 5.35 grams of 2-methylaniline precooled to 0-5 °C was added slowly over about 50 minutes maintaining the 0-5 °C range. An additional 10 minute (one-hour elapsed time) was allowed for the formation of the amine chloride. A precooled solution (0-5 °C) of 3.5 grams of sodium nitrite, $NaNO_2$ in 8 mL of water, was then added over about 50 minutes maintaining the 0-5 °C range. The reaction was allowed to complete in the next 70 minutes, 2 hours from the beginning of $NaNO_2$ addition. A precooled solution (0-5 °C) of 19 grams of $SnCl_2$ in 15 mL of 31% by weight HCl plus 35 mL of water (about 50 mL total), was added slowly over the next 2 hours maintaining the 0-5 °C range. The reaction was then allowed to complete for the next hour. The precipitate was filtered, and the filter cake washed with 15 mL of a solution of 4.5 mL of 31% by weight HCl plus 10.5 mL of water. The cake was vacuum dried at about 40 °C. Final product of 7.01 grams weight was obtained for 88% yield.

Example 2. The Production of the 2-Methylphenylhydrazine Hydrochloride from 0.1 Gram-Moles of 2-Methylaniline The reaction was sized for a 500 mL reaction flask fitted with a magnetic stirrer. The flask was cooled with a −10 °C to −15 °C bath. The reaction was carried out in the range of 0-5 °C, never exceeding 5 °C. The quantities of 64 mL of concentrated (31% by weight) HCl and 36 mL of water were added to the flask. All subsequent additions were made below the surface to the liquid in the reactor near the stirrer. When the temperature reached about 2 °C, 10.7 grams of 2-methylaniline precooled to 0-5 °C was added slowly over about 50 minutes maintaining the 0-5 °C range. An additional 10 minute (one-hour elapsed time) was allowed for the formation of the amine chloride. A precooled solution (0-5 °C) of 6.9 grams of sodium nitrite, $NaNO_2$ in 16 mL of water, was then added over about 50 minutes maintaining the 0-5 °C range. The reaction was allowed to complete in the next 70 minutes, 2 hours from the beginning of $NaNO_2$ addition. A precooled solution (0-5 °C) of 38 grams of $SnCl_2$ in 30 mL of 31% by weight HCl plus 70 mL of water (about 100 mL total), was added slowly over the next 2 hours maintaining the 0-5 °C range. The reaction was then allowed to complete for the next hour. The precipitate was filtered, and the filter cake washed with 30 mL of a solution of 9 mL of 31% by weight HCl plus 21 mL of water. The cake was vacuum dried at about 40 °C. Final product of 10.3 grams was obtained for 65% yield.

The reduced yield in Example 2 indicates the desirability of the internal cooling as the reaction is increased in amounts to be reacted. The change in the surface to volume ratio between the 250 mL and 500 mL flasks indicates that heat transfer control locally throughout the reactor is preferred for high yields.

Example 3. The Production of the 2-Methylphenylhydrazine from 2-Methylphenylhydrazine Hydrochloride About 160 mL of a 25% solution of sodium hydroxide, NaOH, was placed in a 500 mL flask outfitted with stirring and heating. Next, 63 grams of the 2-methylphenylhydrazine hydrochloride was added with stirring to the NaOH solution. The temperature was set to about 45 °C. After 30 minutes, heating was stopped, and 150 mL of room temperature toluene was added with stirring. The stirring was stopped, and the layers allowed to separate. The layers were separated by gravity separation. Next, 4 grams of anhydrous $Na_2SO_4$ was added to the toluene solution. The solution was mixed for 30 minutes to allow the $Na_2SO_4$ hydrate to settle. The solution was filtered to collect the filtrate and the filter cake washed with about 15 mL of toluene. The product is the solution of 2-methylphenylhydrazine in toluene. The 2-methylphenylhydrazine solution was measured by GC/MS to contain 42-44 grams of the 2-methylphenylhydrazine. The yield was 86-90%.

Example 4. The Production of the Iminohydrazone Precursor to the Catalyst from 2-Methylphenylhydrazine A 3-liter reaction vessel was used with a distillation column for reflux and subsequent distillation when the reaction is completed. The vessel had stirring and heating. About 700 grams (800 mL) of toluene was added to the reaction flask. Next, 21 grams of 2-pyrrolidone, $C_4H_7NO$, was added. Next, 31 grams of dimethyl sulfate was added. The flask was heated with stirring for 4 hours at 80 °C. The heating was stopped, and the vessel and contents allowed to cool to room temperature. Then, 30 grams of 2-methylphenylhydrazine dissolved in 150 grams of toluene was added. The vessel was heated for 5 hours at 80 °C with stirring. The heating was stopped, and the vessel was cooled to room temperature. Vacuum was applied at 20-30 Torr pressure while the temperature was maintained at about 20 °C. The solvent was removed until about 200 mL of volume was left in the flask. The distillation was stopped, and 300 mL of ethyl acetate was added. The precursor product is the solid that recovered by filtration. The filter cake was washed with about 40 mL of additional ethyl acetate. The filtrate was saved for recovery. The product is vacuum dried to constant weight. The weight of the solids after drying were 43 grams.

Example 5. The Production of the NHC Catalyst from the Iminohydrazone Precursor

A 1-liter reactor was fitted with a distillation column and connection to a receiver through a condenser such that it can be used for vacuum distillation. The reactor was fitted with stirring and a means of providing controlled heat. The amount of 600 grams (about 700 mL) of toluene was added to the reactor. Next, 43 grams of the iminohydrazone precursor from stage 3 was added. Next, 80 grams of trimethylorthoformate (TMOF) was added. Heat was applied to maintain about 100 °C and a good reflux of the TMOF and toluene. The reaction was continued for 18 hours. At this time the system was switched to distillation and 450 mL of the combined toluene and excess TMOF removed. After the distillation was completed and the system cooled to ambient temperature, 250 mL of ethyl acetate was added. The solids formed were filtered and washed on the filter with 50 mL of additional ethyl acetate. The solid product was dried under vacuum. The filtrate was saved for reprocessing to recover the ethyl acetate and toluene. The weight of the products obtained was 37.5 grams.

Example 6. The Use of the NHC Catalyst to Produce Methyl-5-Methyl-2-Furoate

A 22 L reaction vessel was used with three necks. It was fitted with a heating mantle and jacket. The central neck has a stirring apparatus, and the blade was wide enough to sweep the bottom of the vessel. One neck was fitted with a thermocouple that was connected to heat control electronics for the heating mantle. The other neck was fitted with a distillation column. A joint at the top of the reflux condenser contained a thermocouple for measuring the vapor temperature leading to a cooling condenser. The cooling condenser led to a receiver that was connected to a vacuum distillation source. An amount of 12.54 kg of a solution of 1.18 kg 5-chloromethyl-2-furfuraldehyde (CMF) in toluene was added to the reaction vessel. The stirring was begun and 1,040 grams of anhydrous sodium carbonate, $Na_2CO_3$, was added. Next, 400 grams of methanol was added. Next, 11.7 grams of the NHC catalyst of Formula 1 was added. The temperature of the mixture was increased to 80-81 °C and the reaction continued for 4 hours. At the end of this time the toluene and excess methanol were removed by fractional vacuum distillation using a vacuum pressure of 20-30 Torr starting at 20 °C and completing the distillation of the methyl-5-methyl-2-furoate fraction at 120-130 °C. The methyl-5-methyl-2-furoate was recovered in the last fractions. The last fractions were redistilled to produce methyl-5-methyl-2-furoate at 99% purity as measured by GC/MS analysis. At the end of the reaction, 1,070 grams of the furoate was produced and 1,010 grams was recovered. This was a 93% yield, higher than the usual range for the other NHC catalysts.

The present invention has been described in connection with various example embodiments. It will be understood that the above descriptions are merely illustrative of the applications of the principles of the present invention, the scope of which is to be determined by the claims viewed in light of the specification. Other variants and modifications of the invention will be apparent to those skilled in the art.

The invention claimed is:

1. A method for the synthesis of the N-Heterocyclic Carbene catalyst salt of Formula 1, the method comprising the steps of: (i) contacting a 2-methylphenylhydrazine solution with the reaction products of 2-pyrrolidine and dimethylsulfate to make iminohydrazone of Formula 2 in an organic solvent; (j) distilling the solution of the iminohydrazone of Formula 2 to remove excess solvents; (k) recovering the iminohydrazone of Formula 2 as a solid salt; (l) contacting the iminohydrazone salt of Formula 2 with an organic solvent and trimethylorthoformate to make methylsulfate salt of the N-Heterocyclic Carbene catalyst of Formula 1; (m) recovering the N-Heterocyclic Carbene catalyst of Formula 1 as a salt.

2. The method of claim 1, further comprising, before step (i), the steps of: (e) contacting 2-methylphenylhydrazine hydrochloride salt with an aqueous base to form free 2-methylphenylhydrazine; (f) extracting the 2-methylphenylhydrazine from the aqueous basic solution with an organic solvent to provide a solution of the 2-methylphenylhydrazine in the organic solvent; (g) drying the solution of 2-methylphenylhydrazine by addition of a drying agent; (h) removing the drying agent by filtration; prior to the step of (i) contacting 2-methylphenylhydrazine solution with the reaction products of 2-pyrrolidine and dimethylsulfate to make iminohydrazone of Formula 2 in an organic solvent.

3. The method of claim 2, the method further comprising, before step (e), the steps of: (a) contacting 2-methylaniline with aqueous hydrochloric acid to form the amine chloride; (b) contacting the amine chloride in solution with a diazotization reagent to form the diazonium chloride salt; (c) adding a reducing agent to convert the diazonium chloride salt to 2-methylphenylhydrazine hydrochloride; (d) filtering to recover the 2-methylphenylhydrazine hydrochloride salt as a solid, and using the recovered 2-methylphenylhydrazine hydrochloride salt in step (e).

4. A method as in claim 3, wherein the diazotization reagent is sodium nitrite (NaNO2).

5. A method as in claim 3, wherein the reducing agent is stannous dichloride.

6. A method as in claim 3, wherein the temperature in steps (a), (b) and (c) is maintained locally, where locally means 250 cc volume increments, throughout the reactor between about 0 degrees C and about 5 degrees C.

7. A method as in claim 3, wherein the temperature in step (i) is about 60 degrees C to about 80 degrees C.

8. A method as in claim 3, wherein and the temperature in step (l) is about 80 degrees C to about 100 degrees C.

9. A method as in claim 3, wherein the solvent in steps (f), (i) and (l) is an aromatic hydrocarbon.

10. A method as in claim 3, wherein the solvent in steps (f), (i) or (l) is selected from the group of toluene, a mixture of xylenes, m-xylene, o-xylene, p-xylene.

11. The method of claim 3, wherein tin salts are recovered from the filtrate after step (d) by neutralization with a hydroxide base to produce stannic hydroxide which is subsequently filtered and dried to produce stannic oxide (SnO2) for reprocessing to tin and subsequently to the stannous dichloride.

12. The method of claim 3, wherein the temperature in step (l) is about 60 degrees C to about 100 degrees C; the solvent in steps (i) and (l) is an aromatic hydrocarbon; the diazotization reagent is sodium nitrite (NaNO2); and the reducing agent is stannous dichloride.

13. The method of claim 1, wherein the temperature in step (l) is about 60 degrees C to about 100 degrees C.

14. The method of claim 1, wherein the solvent in steps (i) and (l) is an aromatic hydrocarbon.

15. The method of claim 14, wherein the solvent in step (i) is selected from the group of toluene, a mixture of xylenes, m-xylene, o-xylene, p-xylene.

16. The method of claim 14, wherein the solvent in step (l) is selected from the group of toluene, a mixture of xylenes, m-xylene, o-xylene, p-xylene.

17. The method of claim 1, wherein the temperature in step (l) is about 60 degrees C to about 100 degrees C; the solvent in steps (i) and (l) is an aromatic hydrocarbon.

18. The method of claim 17, wherein the temperature in step (l) is about 60 degrees C to about 100 degrees C; the solvent in step (i) is selected from the group of toluene, a mixture of xylenes, m-xylene, o-xylene, p-xylene.

19. The method of claim 17, wherein the temperature in step (l) is about 60 degrees C to about 100 degrees C; the solvent in step (l) is selected from the group of toluene, a mixture of xylenes, m-xylene, o-xylene, p-xylene.

20. The method of claim 1, wherein the solvent in step (i) is acetonitrile.

* * * * *